United States Patent [19]

Wania et al.

[11] Patent Number: 4,677,068
[45] Date of Patent: Jun. 30, 1987

[54] PROCESS FOR OBTAINING CHOLESTEROL ESTERASE

[75] Inventors: Wolfgang Wania, Sindelsdorf; Jürgen Wahl, Schlehdorf; Maximilian Kellner, Seehausen, all of Fed. Rep. of Germany

[73] Assignee: Boehringer Mannheim GmbH, Mannheim, Fed. Rep. of Germany

[21] Appl. No.: 795,632

[22] Filed: Nov. 6, 1985

[30] Foreign Application Priority Data

Dec. 24, 1984 [DE] Fed. Rep. of Germany ....... 3447390

[51] Int. Cl.$^4$ ........................... C12N 9/18; C12R 1/38
[52] U.S. Cl. ..................................... 435/197; 435/874
[58] Field of Search ........................ 435/197, 249, 248

[56] References Cited

U.S. PATENT DOCUMENTS 3,772,152  11/1973  De Baynast ................... 435/249 X
4,011,138  3/1977   Terada et al. ................. 435/197
4,476,223  10/1984  Buschek et al. ................ 435/188

Primary Examiner—Lionel M. Shapiro
Attorney, Agent, or Firm—Felfe & Lynch

[57] ABSTRACT

The present invention provides a process for obtaining cholesterol esterase by culturing an appropriate microorganism in an appropriate nutrient medium and recovering the enzyme from the culture broth or from the biomass, wherein the culturing is carried out in a mineral salt medium containing n-alkanes with 10 to 20 carbon atoms as the sole source of carbon and in the form of an aerated submersion culture.

13 Claims, 1 Drawing Figure

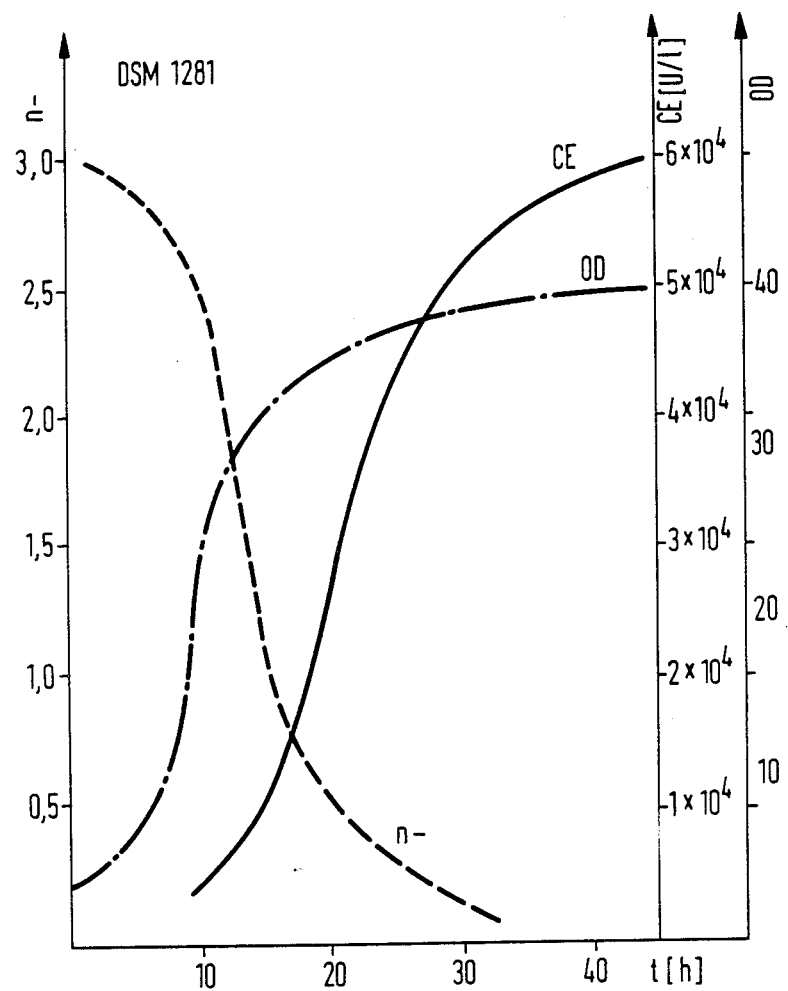

PROCESS FOR OBTAINING CHOLESTEROL ESTERASE

The present invention is concerned with a process for obtaining cholesterol esterase from micro-organisms.

Cholesterol esterase has played an important part in clinical analysis ever since processes have been developed for the enzymatic determination of cholesterol.

Since a large part of cholesterol in biological material is present in the form of esters, the simultaneous use of cholesterol esterase and cholesterol-oxidising enzymes, such as cholesterol oxidase or cholesterol dehydrogenase, also makes possible a completely enzymatic determination of cholesterol esters (see Federal Republic of Germany Patent Specification No. 22 64 847).

The enzyme from micro-organisms has thereby proved to be especially suitable in the scope of cholesterol determinations with cholesterol esterase (see Federal Republic of Germany Patent Specification No. 25 06 712.3).

In the case of the known processes, culturing normally takes place in a nutrient medium which contains an inductor (cf. European Patent Specification No. 0024345 B 1). By "inductor" there is hereby to be understood a substance which stimulates the micro-organism to form the desired enzyme or to form it in larger amounts than without the inductor. Normally, micro-organisms do not require any cholesterol esterase since sufficient other sources of nutrition are available to them and, therefore, they have no need to utilise cholesterol esters. Therefore, inductors are usually cholesterol esters or chemically similar compounds.

It is also already known that in the case of the use of inductors which are chemically remote from cholesterol esters, increased enzyme activities can also be achieved.

However, if known inductors are also used as a source of carbon and especially as the sole source of carbon, the yields of cholesterol esterase are comparatively low.

A further problem of the known processes resides in down stream prozesses of the final fermented culture broth.

All known inductors are substantially water-insoluble and are not completely utilised. This makes it necessary to remove the inductor residues by extraction with organic solvents or the like, which has a serious negative influence on the stability of the purified enzyme.

Therefore, it is an object of the present invention to overcome the disadvantages of the known processes and to provide a process which, with a single source of carbon and without special inductors makes possible better enzyme yields than the known processes. Furthermore, it is an object of the present invention to provide such a process in the case of which the down stream is simplified and does not require an extraction with organic solvents.

Thus, according to the present invention, there is provided a process for obtaining cholesterol esterase by culturing an appropriate micro-organism in an appropriate nutrient medium and recovering the enzyme from the culture broth or from the biomass, wherein the culturing is carried out in a mineral salt medium containing n-alkanes with 10 to 20 carbon atoms as the sole source of carbon and in the form of an aerated submersion culture.

The culturing can be carried out not only in a batch process but also in a partly or completely continuous operation, in one or more steps. For this purpose, there can be used not only a chemostatic but also a turbidostatic operation.

When carrying out the process according to the present invention, the micro-organisms are first adapted in the usual manner to the culture medium which, according to the present invention, contains n-alkanes as the sole source of carbon in that they are cultured in cultures of increasingly larger volume. As a rule, they are first cultured on a solid nutrient agar, then preferably multiplied in complete medium in a shake culture and thereafter inoculated over into the mineral salt medium according to the present invention containing n-alkanes. In this pre-culture, it is preferable to continue culturing until a cholesterol esterase activity of at least 5000 U/liter is achieved.

In the main culture, the temperature is preferably of from about 15° to 45° C., it being especially preferred to operate at a temperature of from 25° to 35° C. Maximum enzyme yields are generally obtained under these conditions in the case of a culturing period of from 2 to 5 days but in many cases a culturing period of 2 to 3 days suffices. The cholesterol esterase thereby occurs not only in the medium but also in the cells. By increasing the period of culturing, the ratio of the enzyme activity in the biomass to the enzyme activity in the culture broth is displaced in favour of the latter until, finally, the total activity is present in the culture broth. Therefore, according to a preferred embodiment of the present invention, the culturing is carried out until practically all the activity is present in the culture broth and is thereafter isolated from the culture filtrate and can then, if desired, be purified.

The transfer of the activity into the culture broth can be accelerated, for example, by changing the pH, changing the culturing temperature or by the addition of surface-active substances.

As a rule, the n-alkane concentration in the culture medium is maintained in the range of from 0.1 to 5% v/v. However, it is possible to go above or below these values which, however, does not provide any advantages.

The pH value is preferably maintained, by the addition of an appropriate correction agent, at a value of from about 5 to 9 and preferably of from 6 to 8.

An especially preferred nutrient medium according to the present invention contains, apart from the n-alkanes, also the following salts, referred to 1000 liters (1 m$^3$):

- 5 to 10 kg., preferably 6 to 8 kg. diammonium hydrogen phosphate,
- 1 to 5 kg., preferably 2 to 4 kg. potassium dihydrogen phosphate,
- 0.2 to 2 kg., preferably 0.8 to 1.2 kg. magnesium sulphate,
- 0.2 to 2 kg., preferably 0.8 to 1.2 kg. calcium chloride,
- 0.01 to 0.5 kg., preferably 0.03 to 0.15 kg. sodium chloride,
- 0.1 to 1 liter of 1% ferric chloride solution,
- 0.1 to 1 liter of 0.2% cupric chloride solution,
- 0.01 to 1 liter of 1% zinc sulphate solution, as well as traces of the elements manganese, cobalt, molybdenum and boron.

As micro-organisms, there can, in principle, be used those which provide a content of cholesterol esterase making working up worthwhile. A comparatively large number of micro-organisms is known, for example, from Federal Republic of Germany Patent Specification No. 25 06 712. Within the scope of the present invention, it is preferred to use Pseudomonas spec. DSM 1280 and DSM 1281.

With n-alkane, the best results are obtained with those compounds or mixtures which contain straight-chained n-alkanes with 14 to 18 carbon atoms, thus especially with n-tetradecane, n-hexadecane and n-octadecane.

The following Example is given for the purpose of illustrating the present invention, with reference to the accompanying drawing, in which the decrease of the n-alkane in the medium, the increase of micro-organism density (OD) and of enzyme activity in the culture broth are plotted against time.

EXAMPLE

1. Nutrient medium:

| raw materials | main fermentate (kg./1 m³) |
|---|---|
| diammonium hydrogen phosphate | 7.0 |
| potassium dihydrogen phosphate | 3.0 |
| magnesium sulphate heptahydrate | 0.6 |
| sodium chloride | 0.05 |
| ferric chloride hexahydrate (1%) | 0.1 liter |
| zinc sulphate heptahydrate (1%) | 0.1 liter |
| calcium chloride | 1.0 |
| n-hexadecane (95%) (olefin-free) | 30.0 |
| drinking water | 1 m³ |
| pH (adjusted with phosphoric acid before sterilisation) | 6.6 |

2. Initial and pre-culturing

Tilted agar cultures of Pseudomonas sp. DSM 1281 are cultured for 72 hours at 30° C. and subsequently kept at 4° C. The composition of the nutrient medium is as stated above under (a).

A. Liquid carrying out:

100 ml. of nutrient medium as described in (1) and 0.2% (w/v) of yeast extract in a 300 ml. shaking flask are inoculated with a loop of the tilted agar culture and incubated at 30° C. for 72 hours at 130 r.p.m.

B. Liquid carrying out:

Four 1 liter shaking flasks, each with 250 ml. of culture medium, are inoculated with the A liquid culture in a ratio of 1:100 and shaken for 72 hours at 30° C. and 130 r.p.m. The pH value is then 7.5 to 8.0 and the cholesterol esterase activity is about 5000 U/liter.

This liquid culture serves as an inoculation culture for a 10 liter fermenter.

C. Pre-fermentation:

Use is made of a 10 liter fermenter equipped with 4 baffle plates and 3 disc stirrers. The inoculum amounts to 1%. The running time of the pre-fermentation is about 24 to 48 hours. The cholesterol esterase activity is then about $6 \times 10^4$ U/liter.

D. Main fermentation

Use is made of a 1 m³ fermenter equipped with 3 disc stirrers, 4 baffle plates and a mechanical foam breaker. Drinking water is used as the process water. All the components of the nutrient medium are dissolved in the fermenter and sterilised. The n-hexadecane is sterilised separately with about 10% by volume of drinking water and added aseptically to the nutrient medium at a temperature above 20° C. The fermentation is carried out for 20 to 50 hours at 20° to 37° C. and at 250 to 400 r.p.m. and 0.5 to 1.5 VVM air introduction. The course of the fermentation is graphically illustrated in the accompanying drawing. The yield of cholesterol esterase is of the order of $6.5 \times 10^4$ U/liter.

We claim:

1. In a process for obtaining cholesterol esterase enzyme by culturing a micro-organism which produces cholesterol esterase in a nutrient medium for said micro-organism and recovering the enzyme from the culture broth or from the biomass, the improvement wherein the culturing is carried out in an aerated submersion culture with a mineral salt medium containing n-alkanes having 10 to 20 carbon atoms as the sole source of carbon.

2. The process of claim 1, wherein culturing is carried out for 2 to 5 days at 15° to 45° C.

3. The process of claim 2, wherein culturing is carried out until substantially all of the enzyme activity is present in the culture broth.

4. The process of claim 1, wherein the n-alkane concentration in the nutrient medium is from 0.1 to 5% v/v.

5. The process of claim 1 further comprising culturing the micro-organism in a pre-culture on an n-alkane-containing medium until a cholesterol esterase activity of at least 5000 U/liter is achieved and thereafter culturing the micro-organism is said submersion culture.

6. The process of claim 1, wherein the n-alkane is one containing 14 to 18 carbon atoms or a mixture thereof.

7. The process of claim 1, wherein a pH of 5 to 9 is maintained during the culturing.

8. The process of claim 7, wherein the pH is maintained by the use of a phosphate buffer.

9. The process of claim 1 wherein the salts contain ammonium, iron, copper, zinc, calcium and magnesium ions.

10. The process of claim 1 wherein the micro-organism is Pseudomonas sp. DSM 1280 or 1281.

11. The process of claim 7 wherein the n-alkane concentration is 0.1 to 5% by volume.

12. The process of claim 1 wherein, the culture medium is at a temperature of 15° to 45° C., a pH of about 5 to 9 and contains 0.1 to 5% by volume of the n-alkane having 10 to 20 carbon atoms, and, in each 1000 liters, the culture medium further contains 5 to 10 kg. diammonium hydrogen phosphate,
1 to 5 kg potassium dihydrogen phosphate,
0.2 to 2 kg magnesium sulphate,
0.2 to 2 kg calcium chloride,
0.01 to 0.5 kg sodium chloride,
0.01 to 1 liter of 1% ferric chloride solution,
0.1 to 1 liter of 0.2% cupric chloride solution,
0.01 to 1 liter of 1% zinc sulphate solution, as well as traces of the elements manganese, cobalt, molybdenum and boron.

13. The process of claim 12 wherein the micro-organism is Pseudomonas sp. DSM 1280 or 1281.

* * * * *